US005767287A

United States Patent [19]

Bobrow et al.

[11] Patent Number: 5,767,287
[45] Date of Patent: Jun. 16, 1998

[54] COMPOUNDS AND METHOD FOR SYNTHESIZING SULFOINDOCYANINE DYES

[75] Inventors: Mark Norman Bobrow, Lexington; Thomas Joseph Erickson, Carlisle, both of Mass.

[73] Assignee: E. I. du Pont de Nemours and Company, Wilmington, Del.

[21] Appl. No.: 869,032

[22] Filed: Jun. 4, 1997

Related U.S. Application Data

[62] Division of Ser. No. 687,853, Jul. 26, 1996, Pat. No. 5,688,966.
[51] Int. Cl.$^6$ .................................................. C07D 209/08
[52] U.S. Cl. ................................................................ 548/455
[58] Field of Search ............................................... 548/455

[56] References Cited

U.S. PATENT DOCUMENTS

| | | | |
|---|---|---|---|
| 4,948,882 | 8/1990 | Ruth | 536/27 |
| 4,981,977 | 1/1991 | Southwick et al. | 548/455 |
| 5,106,990 | 4/1992 | Ohno et al. | 548/427 |
| 5,196,306 | 3/1993 | Bobrow et al. | 435/7.9 |
| 5,268,486 | 12/1993 | Waggoner et al. | 548/427 |
| 5,486,616 | 1/1996 | Waggoner et al. | 548/217 |

OTHER PUBLICATIONS

Mujumdar, R.B., Ernst, L.A., Mujumdar, S.R., Lewis, C.J. and Waggoner, A.S., Cyanine Dye Labeling Reagents: Sulfoindocyanine Succinimidyl Esters, *Bioconjugate Chemistry*, 4, 105–111, 1993.

Chao, J., DeBiasio R., Zhu, Z. Giuliano, K.A., and Schmidt, B.F., Immunofluorescence Signal Amplification by the Enzyme-Catalyzed Deposition of a Fluorescent Reporter Substrate (Card), *Cytometry*, 23, 48–53, 1996.

Livaniou, E., Evangelatos, G.P., and Ithakissios, D., Radio-iodinated Biotin Derivatives for In Vitro Radioassays, *The Journal of Nuclear Medicine*, 28, 1430–1434, 1987.

Livaniou, E., Evangelatos, G.P., Ithakissios, D.S., Biotin Radioligand Assay with an $^{125}$I-Labeled Biotin Derivative, Avidin, and Avidin Double-Antibody Reagents, *Clinical Chemistry*, 33, 1983–1988, 1987.

Evangelatos, A.S., Livaniou, E. Kakabakos, S.E., Evangelatos, G.P., and Ithakissios, D.S., Biotinidase Radiassay Using an $^{125}$I-Biotin Derivative, Avidin, and Polyethylene Glycol Reagents, *Analytical Biochemistry*, 196, 385–389, 1991.

*Primary Examiner*—Joseph McKane

[57] ABSTRACT

Novel intermediates having an indolenine nucleus which are useful in the synthesis of fluorescent sulfoindocyanine dyes are described. Dyes synthesized using such intermediates do not contain a reactive group that will covalently attach to a target molecule at an amine- or hydroxy-containing site. Rather, these intermediates are linked to an enzyme substrate or a member of a specific binding pair. Also included are tyramide-containing sulfonidocyanine dyes.

3 Claims, 1 Drawing Sheet

COMPOUNDS AND METHOD FOR SYNTHESIZING SULFOINDOCYANINE DYES

This is a division of application Ser. No. 08/687,853, filed Jul. 26, 1996 now U.S. Pat. No. 5,688,966.

FIELD OF THE INVENTION

This invention relates to fluorescent sulfoindocyanine dyes and, more particularly, to compounds having an indolenine nucleus and method utilizing such compounds to make sulfoindocyanine dyes.

BACKGROUND OF THE INVENTION

Use of fluorescent labels with antibodies, DNA probes, biochemical analogs, lipids, drugs, cytokines, cells and polymers has expanded rapidly in recent years due, in part, to the availability of new fluorescent labeling reagents.

Mujumdar et al., Bioconjugate Chemistry, Vol. 4, pages 105–111 (1993) describes a series of fluorescent labeling reagents based on sulfoindocyanine dyes. They contain succinimidyl ester reactive groups and can be readily conjugated to antibodies, avidin, DNA, lipids, polymers, and other amino-group containing materials. These sulfoindocyanine dyes generally are formed when a quaternized indolenine nucleus containing a carboxyl alkyl group for later activation of the fluorophore is linked to a second identical (or different) indolenine nucleus through a polymethine chain of three, five or seven conjugated methine carbon atoms.

Chao et al., Cytometry, Vol. 23, pages 48–53 (1996), describes a fluorescent horseradish peroxidase substrate, Cy3.29 and its use in an enzyme-based signal amplification system (catalyzed reporter deposition, CARD). Cy3.29 tyramide was synthsized by utilizing a succininide ester intermediate.

U.S. Pat. No. 4,981,977, issued to Southwick et al. on Jan. 1, 1991, describes intermediates for and fluorescent cyanine dyes containing carboxylic acid groups.

U.S. Pat. No. 5,268,486, issued to Waggoner et al. on Dec. 7, 1993, describes a method for labeling and detecting materials employing arylsulfonate cyanine dyes.

Similarly, U.S. Pat. No. 5,486,616, issued to Waggoner et al. on Jan. 23, 1996, describes a method for labeling and detecting materials employing arylsulfonate cyanine dyes.

U.S. Pat. No. 5,106,990, issued to Ohno et al. on Apr. 21, 1992, describes indolenine derivatives as dyes.

U.S. Pat. No. 4,948,882, issued to Ruth on Aug. 14, 1990, describes single-stranded labelled oligonucleotides, reactive monomers and methods of synthesis.

SUMMARY OF THE INVENTION

The present invention concerns a compound having an indolenine nucleus for synthesizing a sulfoindocyanine dye, said compound having the structure:

wherein

X is selected from the group consisting of $CH_3$—C—$CH_3$, O and S;

Z is a linkage group through which the indolenine nucleus is linked to A; and

A is selected from the group consisting of an enzyme substrate and a member of a specific binding pair.

In a second embodiment the invention concerns sulfoindocyanine dyes having the structure:

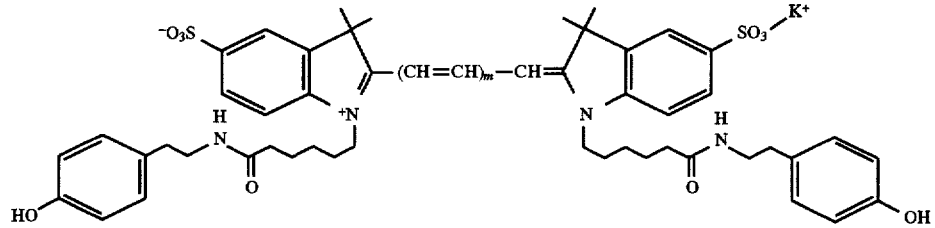

wherein m is 1, 2 or 3.

In a third embodiment the invention concerns a process for making a sulfoindocyanine dye which comprises reacting a) a first compound having an an indolenine nucleus, said compound having the structure:

wherein

X is selected from the group consisting of $CH_3$—CH—$CH_3$, O and S;

Z is a linkage group through which the indolenine nucleus is linked to A; and

A is selected from the group consisting of an enzyme substrate and a member of a specific binding pair;

b) a second compound having an indolenine nucleus which is the same or different from the first compound; and c) a reagent for linking the first compound to the second compounds;

wherein said first and second compounds and reagent are reacted in a weakly basic solvent at reflux for at least one hour.

In a fourth embodiment the invention concerns a sulfoindocyanine dye made utilizing the compound having an indolenine nucleus.

DETAILED DESCRIPTION OF THE INVENTION

Figure 1:
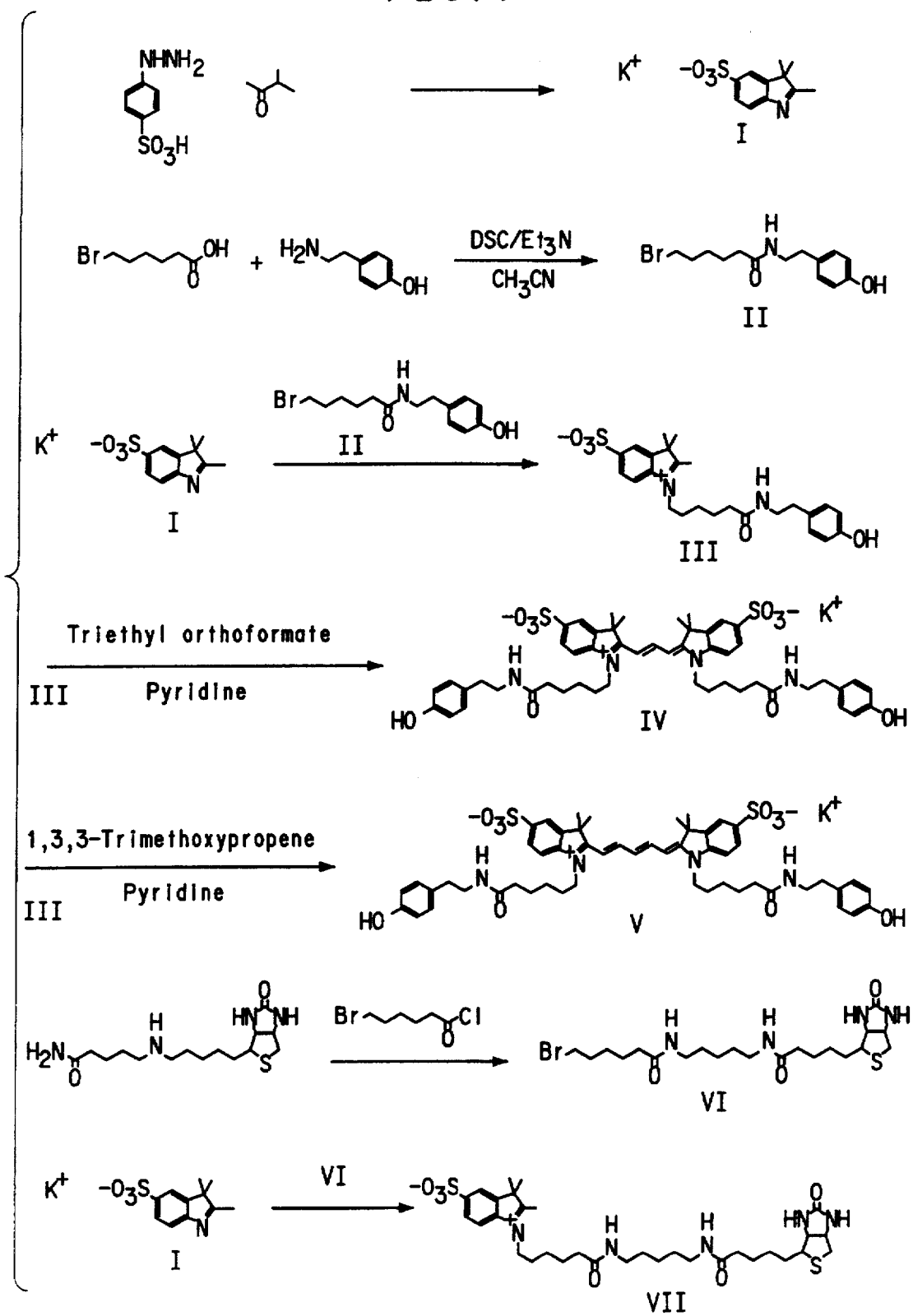
FIG. 1 depicts the synthesis of compounds having an indolence nucleus and their use in synthesizing sulfoindocyanine dyes.

The present invention relates to novel intermediates having an idolenine nucleus which are useful in synthesizing sulfoindocyanine dyes which do not contain a reactive group that will covalently attach to a target molecule at a site such as an amine- or hydroxy-containing site. Rather, these intermediates are linked to an enzyme substrate or a member of a specific binding pair.

More specifically, these intermediates are compounds having an indolenine nucleus and can be used to synthesize a sulfoindocyanine dye, said compound having the structure:

wherein

X is selected from the group consisting of $CH_3$—C—$CH_3$, O and S;

Z is a linkage group through which the indolenine nucleus is linked to A; and

A is selected from the group consisting of an enzyme substrate and a member of a specific binding pair.

Examples of linkage groups for linking Z to A, include but are not limited to, —$(CH_2)_5$—C(O)—NH—$(CH_2)_2$—, alkyl, alkenyl or alkynyl groups which can be unsubstituted or substituted with a substitutent, including but not limited to, an ether group, ester, amide, thioether (sulfide), sulfonamide, urea, thiourea, urethane or phosphate ester.

The preferred linkage group is —$(CH_2)_5$—(C(O))—NH—$(CH_2)_2$—.

Suitable enzyme substrates include but are not limited to phenolic groups such as tyramine, and other groups such as thiophosphates, or 3-methyl-2-benzothiazolinone hydrazone (MBTH).

Members of specific binding pairs can be of the immune or nonimmune type. Immune specific binding pairs are exemplified by antigen/antibody systems or hapten/antihapten systems. The antibody member, whether polyclonal or monoclonal or an immunoreactive fragment thereof, of the binding pair can be produced by customary methods familiar to those skilled in the art. The terms "immunoreactive antibody fragment" or "immunoreactive fragment" mean fragments which contain the binding region of the antibody. Such fragments may be Fab-type fragments which are defined as fragments devoid of the Fc portion, e.g., Fab, Fab', and F(ab')$_2$ fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc.

The process of the invention comprises reacting a) a first compound having an an indolenine nucleus, said compound having the structure:

wherein

X is selected from the group consisting of $CH_3$—C—$CH_3$, O and S;

Z is a linkage group through which the indolenine nucleus is lined to A; and

A is selected from the group consisting of an enzyme substrate and a member of a specific binding pair;

b) a second compound having an indolenine nucleus which is the same or different from the first compound; and c) a reagent to link the first compound to the second compound;

wherein said compounds and reagent are reacted in a weakly basic solvent at reflux for at least one hour.

As illustrated in the Examples below, symmetrical dyes are synthesized by reacting the same compounds having an indolenine nucleus with a reagent for linking the compounds together in a weakly basic solvent at reflux for at least one hour. The structure of these compounds is depicted above.

Asymmetrical dyes are synthesized in the same manner as the symmetrical dyes except that the second compound is different from the first compound. For example, the second compound can have the following structure:

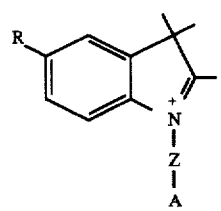

wherein R can be sulfonate or hydrogen and Z and A are as defined above provided that at least one of Z or A is different from Z or A in the first compound.

Reagents suitable for lining the monomers together are those useful in generating a polymethine chain of at least three carbon atoms. Preferred polymethine chains will have three, five, or seven conjugated methine carbon atoms. Examples of suitable reagents include triethylorthoformate and 1, 3, 3-trimethoxypropene.

The term "weakly basic" means that the pH is in the range from about 8 to about 10. Examples of weakly basic solvents are pyridine or an alcohol or other suitable solvent in which potassium acetate can be dissolved.

Tyramide-containing sulfoindocyanine dyes made using the process of the invention can be used as reporter substrates in an enzyme-based signal amplification system called catalyzed reporter deposition ("CARD"). The CARD system constitutes the subject matter of U.S. Pat. No. 5,196,306 which issued to Bobrow et al. on Mar. 23, 1993, the disclosure of which is hereby incorporated by reference. Use of such dyes in connection with the CARD system is described in Chao et al., Cytometry, 23:48–53 (1996).

Structures of tyramide containing sulfoindocyanine dyes which can be synthesized using the above-described process include:

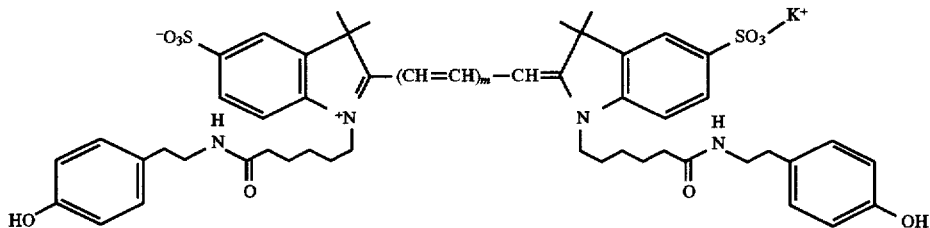

wherein m is 1, 2 or 3.

Also included are sulfoindocyanine dyes made using the process of the invention.

The following examples are intended to illustrate the invention. These examples are also depicted in FIG. 1.

EXAMPLE 1 a) 2,3,3-Trimethyl-3 H-indole-5-sulfonic acid, potassium salt (I)

A mixture of p-hydrazinobenzenesulfonic acid (100 g, 0.53 mol) and 3-methyl-2-butanone (168 mL, 1.6 mol) in acetic acid (300 mL) is heated to reflux with mechanical stirring for 3 hours and the reaction mixture is cooled to room temperature, the stirring continued overnight, and filtered to give a pink solid which is then re-dissolved in methanol (750 mL) and precipitated by adding a saturated solution of potassium hydroxide in isopropanol (400 mL). The mixture is filtered and dried in a vacuum oven to give (I) as a yellow/brown cake which is crushed to a fine powder with a mortar and pestle.

$^1$H NMR (D$_2$O) δ 7.84 (s, 1 H, aromatic 4-H), 7.80 (s, 1 H, aromatic 6-H), 7.55 (d, 1 H, aromatic 7-H), 2:33 (s, 3 H, 2-methyl), 1.32 (s, 6 H, 3,3-gem-dimethyl).

b) 6-Bromo-N-[2-(4-hydroxyphenyl)ethyl]-haxanamide (II)

To a solution of 6-bromohexanoic acid (4.51 g, 23.1 mmol) in acetonitrile (50 mL) is added N,N'-disuccinimidyl carbonate (6.5 g, 25 mmol) and triethylamine (3.2 mL, 23 mmol). The solution is stirred at room temperature for 4 hours and tyramine (3.2 g, 23 mmol) is added and stirred continued at room temperature overnight, evaporated in vacuo, re-dissolved in ethyl acetate (100 mL) and washed with water (6×50 mL) and saturated sodium chloride solution (2×25 mL). The ethyl acetate solution is dried with sodium sulfate, filtered, and evaporated in vacuo to give a light brown gum. The crude product is purified by silica gel chromatography to give 6-bromo-N-[2-(4-hydroxyphenyl)-ethyl]-hexanamide (II) as a light amber syrup.

$^1$H NMR (CDCl$_3$) δ 7.5 (br, 1 H, OH), 7.0 (d, 2 H, aromatic 3,5), 6.8 (d, 2 H, aromatic 2,6), 5.8 (br t, 1 H, NH), 3.5 (m, 2 H, CH$_2$N), 3.3 (t, 2 H, CH$_2$Br), 2.7 (t, 2 H, CH$_2$Ph), 2.1 (t, 2 H, δCH$_2$), 1.9 (m, 2 H, δCH$_2$), 1.6 (m, 2 H, γCH$_2$), 1.4 (m, 2 H, βBCH$_2$).

c) 1-[N-[2-(4-Hydroxyphenyl)ethyl]-hexanamide]-2,3,3-trimethyl-5-sulfo-3 H-indolium, inner salt (III)

A suspension of 6-bromo-N-[2-(4-hydroxyphenyl)ethyl]-hexanamide (II) (1.7 g, 5.3 mmol) and 2,3,3-trimethylindoleninium-5-sulfonate (I) (1.2 g, 4.2 mmol) in 1,2-dichlorobenzene (20 mL) is heated to reflux with stirring for 16 hours. The reaction mixture is cooled to room temperature, the dichlorobenzene decanted, the residue washed with 2-propanol (4×20 mL) and dried to give a purple glassy solid. The crude product is purified by silica gel chromatography to give 1-[N-[2-(4-hydroxyphenyl)-hexanamide]-2,3,3-trimethyl-5-sulfo-3H-indolium, inner salt (II).

$^1$H NMR (CD$_3$OD) δ 7.8 (m, 1 H, 4-H), 7.6 (m, 1 H, 6-H), 7.5 (m, 1 H, 7-H), 3.5 (t, 2 H, εCH$_2$), 3.3 (n, CHD$_2$OD+CH$_2$NH), 2.7 (m, 2 H, CH$_2$Ph), 2.2 (t, 2 H, αCH$_2$), 1.6 (m, (6 H, β,γ,δCH$_2$), 1.4 (s, 3 H, 3-CH$_3$), 1.3 (s, 3 H, 3-CH$_3$).

d) 1-[[2-(4-hydroxyphenyl]ethyl-hexanamide]-2-[3-[1-[N-[2-(4-hydroxyphenyl)ethyl]-hexanamide]-1,3-dihyro-3,3-dimethyl-5-sulfo-2H-indol-2-ylidene]-1-propenyl]-3,3-dimethyl-5-sulfo-3H-indolium, inner salt (IV)

A solution of 1-[N-[2-(4-hydroxyphenyl)ethyl]-hexanamide]-2,3,3-trimethyl-5-sulfo-3H-indolium, inner salt (III) (58 mg, 0.12 mmol) is heated to reflux in pyridine (3 mL) and triethyl orthoformate (80 μL, 0.48 mmol) is added via syringe over 1 hour in four equal portions. The purple suspension is then heated to reflux for an additional hour, cooled to room temperature and diethyl ether (15 mL) is added to precipitate the crude product as a purple solid. The solid is subsequently washed with additional diethyl ether (5×15 mL) and purified by HPLC and the isolated product is passed over a 0.4×6 cm column of AG5OW-X4, 200–400 mesh, K$^+$ form, and evaporated to give (IV) as a purple solid.

$^1$H NMR (CD$_3$OD) δ 8.3 (br t, 1 H, position 2 of spacer), 7.9 (m, 4 H, 4,7-H), 7.3 (m, 2 H, 6-H), 7.0 (d, 4 H, 3,5-H, tyramide), 6.5 (d, 4 H, 2,6-H, tyramide), 6.3 (t, 2 H, position 1,3 of spacer), 4.0 (m, 4 H, CH$_2$N), 3.3 (m, 4 H, CH$_2$NH), 2.5 (m, 4 H, CH$_2$Ph), 2.0 (m, 4 H, CH$_2$CO), 1.0–1.8 (m, 24 H, gem-dimethyl+β,γ,δCH$_2$). λ$_{max}$(H$_2$O=550, 517, 278 nm.

EXAMPLE 2

1-[[2-(4-hydroxyphenyl)ethyl]-hexanamide]-2-[3-[1-[N-[2-(4-hydroxyphenyl)ethyl]-hexanamide]-1,3-dihyro-3,3-dimethyl-5-sulfo-2H-indol-2-ylidene|-1,3-pentadienyl]-3,3-dimethyl-5-sulfo-3H-indolium, inner salt (V)

A mixture of 1-[-[2-(4-hydroxyphenyl)ethyl]-hexanamide]-2,3,3-trimethyl-5-sulfo-3H-indolium, inner salt (III) (1 g, 2.1 mmol), potassium acetate (110 mg, 1.05 mmol), and methanol (5 mL) is refluxed as 1,3,3-trimethoxypropene (0.6 mL) is added in four equal portions (0.15 mL each) at intervals of 30 minutes. After the last addition of 1,3,3-trimethoxypropene, the mixture is refluxed for an additional 30 minutes (total reaction time 2.5 hours), potassium acetate is filtered from solution and the filtrate is cooled to 4° C. overnight and the resulting crystalline dye (V) is filtered, washed with 2-propanol, and dried in vacuo.

EXAMPLE 3 a) N-1-Biotinyl-N-5-(6-bromohexanoyl)-pentane diamine (VI)

Biotin cadavarine (21 mg, 0.064 mmol) is dissolved in dimethylformamide (DMF) (1 mL) and triethylamine (10 µL, 0.071 mmol) and 6-bromohexanoyl chloride (11 µL, 0.071 mmol) are added via syringe. After stirring overnight at room temperature, the DMF is evaporated in vacuo and purified by C8 reverse phase chromatography to give (VI) as a white solid.

$^1$H NMR (CD$_3$OD) δ 7.9 (br t, NH), 4.4 (m, 1 H, biotin methine), 4.2 (m, 1 H, biotin methine), 3.4 (t, 2 H, CH$_2$-Br), 3.2 (t, 1 H, CH-S, 3.1 (m, 4 H, CH$_2$-NH), 2.6, 2.8 (m, 2 H, CH$_2$-S), 2.1 (m, CH$_2$-CO), 1.1–1.8 (m, 18 H, internal CH$_2$).

b) 1-[N-[biotinylaminopentylhexanamide]-2,3,3-trimethyl-5-sulfo-3H-indolium, inner salt (VII)

A suspension of N-1-biotinyl-N-5-(6-bromohexanoyl)-pentane diamine (VI) (24 mg, 0.047 mmol) and 2,3,3-trimethyl-3H-indole-5-sulfonic acid, potassium salt (I) (15 mg, 0.054 mmol) in 1,2-dichlorobenzene (1 mL) is heated to 115° C. and stirred under an atmosphere of nitrogen for 16 hours. The suspension is cooled to room temperature, the 1,2-dichlorobenzene is decanted and the residue is dissolved in 25% methanol/water and purified by C8 reverse phase chromatography to give (VII) as a pink solid.

What is claimed is:

1. A process for making a sulfoindocyanine dye which comprises reacting a) a first compound having an an indolenine nucleus, said compound having the structure:

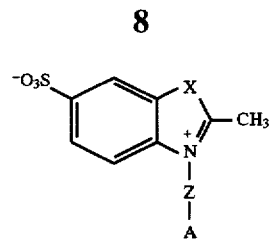

wherein

X is selected from the group consisting of CH$_3$—C—CH$_3$, O and S;

Z is a linkage group through which the indolenine nucleus is linked to A; and

A is selected from the group consisting of an enzyme substrate and a member of a specific binding pair;

b) a second compound having an indolenine nucleus which is the same or different from the first compound; and c) a reagent for linking the first compound to the second compounds;

wherein said first and second compounds and reagent are reacted in a weakly basic solvent at reflux for at least one hour.

2. A process according to claim 1 wherein X is CH$_3$—C—CH$_3$, Z is —(CH$_2$)$_5$—C(O)—NH—(CH$_2$)—, and A is a phenolic group and the structure of the second compound is the same as the structure of the first compound.

3. A sulfoindocyanine dye made according the process of claim 1 or 2.

* * * * *

UNITED STATES PATENT AND TRADEMARK OFFICE
CERTIFICATE OF CORRECTION

PATENT NO.   : 5,767,287
DATED        : June 16, 1998
INVENTOR(S)  : Mark Norman Bobrow, Thomas Joseph Erickson It is certified that error appears in the above-indentified patent and that said Letters Patent is hereby corrected as shown below:

Column 2, line 60, delete "$CH_3\text{-}CH\text{-}CH_3$", and insert -- $CH_3\text{-}C\text{-}CH_3$ --.

Signed and Sealed this

Thirtieth Day of March, 1999

Attest:

Q. TODD DICKINSON

*Attesting Officer*     Acting Commissioner of Patents and Trademarks